United States Patent
Policello et al.

(10) Patent No.: US 6,221,811 B1
(45) Date of Patent: Apr. 24, 2001

(54) SILOXANE NONIONIC BLENDS USEFUL IN AGRICULTURE

(75) Inventors: George Policello, Ossining, NY (US); Peter Stevens, Bellevue Geneva (CH)

(73) Assignee: Crompton Corporation, Greenwich, CT (US)

(*) Notice: Subject to any disclaimer, the term of this patent is extended or adjusted under 35 U.S.C. 154(b) by 0 days.

(21) Appl. No.: 09/026,867

(22) Filed: Feb. 20, 1998

Related U.S. Application Data

(60) Provisional application No. 60/038,599, filed on Mar. 6, 1997.

(51) Int. Cl.⁷ .................................................. A01N 25/22
(52) U.S. Cl. ............................ 504/351; 504/118; 424/405
(58) Field of Search ...................... 424/405, 486; 71/64.1; 514/772; 523/1, 122; 504/351, 118

(56) References Cited

U.S. PATENT DOCUMENTS

| | | | |
|---|---|---|---|
| 5,104,647 | * 4/1992 | Policello | ............................... 514/772 |
| 5,504,054 | 4/1996 | Policello . | |
| 5,558,806 | 9/1996 | Policello . | |
| 5,561,099 | 10/1996 | Murphy . | |
| 5,658,851 | 8/1997 | Murphy . | |
| 5,674,514 | * 10/1997 | Hasslin | ................................. 424/405 |

FOREIGN PATENT DOCUMENTS

| | | |
|---|---|---|
| 0112593 | 7/1984 | (EP) . |
| 0483095 | 4/1992 | (EP) . |
| 8912394 | 12/1989 | (WO) . |

OTHER PUBLICATIONS

Chemical Abstract—52503–47–6.
Chemical Abstract—106:191231.
Chemical Abstract—106:80405.
chemical Abstract—103:89334.
Chemical Abstract—103:66794.
Chemical Abstract—84:43919.
Chemical Abstract—101:67823.
Chemical Abstract—99:83744.
Chemical Abstract—97:74345.

* cited by examiner

Primary Examiner—Peter F. Kulkosky
(74) Attorney, Agent, or Firm—Shirley S. Ma

(57) ABSTRACT

Disclosed are compositions of nonionic siloxane alkoxylates with aminopolyalkyleneoxide surfactants which are useful in treating plants, for instance as adjuvants for pesticides including in particular herbicides. These compositions overcome the antagonism associated with nonionic trisiloxane alkoxylates on pesticide uptake in plants.

10 Claims, No Drawings

SILOXANE NONIONIC BLENDS USEFUL IN AGRICULTURE

This application claims priority from U.S. Provisional Application Ser. No. 60/038,599, filed Mar. 6, 1997.

BACKGROUND OF THE INVENTION

Many pesticides require the addition of an adjuvant to the spray mixture to provide wetting and spreading on foliar surfaces. Often that adjuvant is a surfactant, which can perform a variety of functions, such as increasing spray droplet retention on difficult to wet leaf surfaces, or to provide penetration of the herbicide into the plant cuticle. These adjuvants are either provided as a component in an adjuvant formulation or used as an additive in herbicide formulations.

Trisiloxane alkoxylates are well known for their ability to provide enhanced spreading and wetting properties to pesticide spray solutions, relative to more commonly used organic based (nonsilicone) surfactants. At times it is necessary to include other surfactants in the spray mixture along with the trisiloxane alkoxylate. Unfortunately, the presence of many classes of cosurfactants interfere with the performance of the trisiloxane alkoxylate.

SUMMARY OF THE INVENTION

The present invention teaches a surfactant composition of nonionic siloxane alkoxylates and aminoalkyleneoxide surfactant, and their use as adjuvants, for pesticides. The present invention provides a surfactant composition that gives enhanced wetting of spray solutions on difficult to wet surfaces, such as waxy plants, and enhance the uptake of agrichemicals into plants as compared to more commonly used blends of polyalkyleneoxide/trisiloxane alkoxylate surfactants.

The composition of the present invention is useful as a tank side additive, or as a component in a herbicide formulation. In addition the compositions of the present invention are useful as adjuvants for other pesticides, such as, fungicides, insecticides, plant growth regulators, acaracides and the like.

DETAILED DESCRIPTION OF THE INVENTION

The present invention provides novel surfactant compositions that are useful as adjuvants for pesticides. The compositions of the present invention provide enhanced spray coverage relative to conventional wetting agents. In addition, these products provide a low aqueous surface tension (<23 mN/m at 0.1 wt %), which is necessary and desirable for spreading of pesticide solutions.

Composition

The compositions of the present invention include a nonionic siloxane alkoxylate and an aminopolyalkyleneoxide.

a. Nonionic Siloxane Alkoxylate

The siloxane alkoxylate has the general formula:

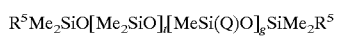

wherein f=0 to 1, preferably 0, g=1 to 2, preferably 1, $Q=C_dH_{2d}O(C_2H_4O)_t(C_3H_6O)_wR^4$, d=2 to 4, preferably 3, t=3 to 12, preferably 4 to 8, w=0 to 8, providing that when w is >0, (t+w) is preferably between 5 and 12. $R^4$ is hydrogen, acetyl or a hydrocarbon radical between 1 and 4 carbon atoms. $R^5$ is Q, alkyl of one to four carbons or a hydroxyl group. The preferred nonionic siloxane alkoxylates are trisiloxane alkoxylates, which have f=0, g=1, d=3, t=4 to 8, w=0, $R^4$ is H or Me.

b. Aminopolyalkyleneoxide

The compositions of the present invention also contain aminopolyalkyleneoxide surfactants which do not detract from the efficacy of the composition. Examples include alkoxylated diamines of the formula $(H(R^T)_T)_2NC_2H_4N((R^T)_TH)_2$ wherein $R^T$ denotes alkoxy groups containing 2 or 3 carbon atoms each, and the subscript T is selected so that the molecular weight of the alkoxylated diamine is 1,000 to 15,000. Preferably, ethoxy units comprise 10 to 90% and more preferably 20 to 50% of the polyalkoxylate chains.

The ratio of the aminopolyalkyleneoxide to the nonionic siloxane alkoxylate is in the range of 99:1 and 1:99 by weight.

The compositions of the present invention also optionally include ingredients for use herein which are pesticides, especially acid functional ones, e.g., compounds that contain at least one carboxylic, sulfonic or phosphonic acid group which is in the form of the free acid or a salt or ester thereof. The term pesticide means any compound used to destroy pests, e.g., insecticides, rodenticides, fungicides, and herbicides, and is also used herein to include plant growth regulatory compounds. Illustrative examples of pesticides which can be employed include, but are not limited to, growth regulators, photosynthesis inhibitors, pigment inhibitors, mitotic disrupters, lipid biosynthesis inhibitors, cell wall inhibitors, and cell membrane disrupters. The amount of pesticide employed in compositions of the invention varies with the type of pesticide employed. More specific examples of pesticide compounds that can be used with the compositions of the invention are: phenoxy acetic acids, phenoxy propionic acids, phenoxy butyric acids, benzoic acids, triazines and s-triazines, substituted ureas, uracils, bentazon, desmedipham, methazole, phenmedipham, pyridate, amitrole, clomazone, fluridone, norflurazone, dinitroanilines, isopropalin, oryzalin, pendimethalin, prodiamine, trifluralin, glyphosate, sulfonylureas, imidazolinones, cyclohexanediones, aryloxyphenoxypropanoates, dichlobenil, isoxaben, and bipyridylium compounds.

Manufacture

The nonionic siloxane alkoxylates, aminoalkyleneoxide surfactants, and pesticides are commercially available and their manufacture is known in the art.

Use

The nonionic siloxane alkoxylates, aminoalkyleneoxide surfactants blends of the present invention, primarily are intended for use in the agricultural field as adjuvants for pesticide, especially acid functional pesticides, containing aqueous end-use formulations. The compositions of the present invention are added directly to a spray tank along with an acid functional pesticide, or as part of a pesticide formulation. They are used in effective amount, that is, an amount which is sufficient to cause the pesticide to function effectively in the formulation. When used as a tankside additive, the compositions of this invention should be present at weight concentrations between 0.01% and 5.0%, preferably between 0.025% and 0.5%, but in "in can" formulations, the compositions of the present invention may be present at concentrations that will deliver between 0.01% and 5.0% to the final use dilution, preferably between 0.025% and 0.5%, of the final use dilution.

The novel nonionic siloxane alkoxylates/aminoalkyleneoxide surfactant compositions of the present invention may also be used generally as surface active agents in aqueous formulation where there is an acid functionalized component, including, but not limited to, surfactants, wetting agents and softeners for textiles, as flowing and leveling agents in coatings, in hair care products and creams for personal care applications and as anti-static agents and softeners for laundry products. Other uses for the present composition will be obvious to those of skill in the art.

EXAMPLES

The following examples are presented to further illustrate and explain the present invention and should not be taken as limiting in any regard. Unless otherwise indicated, all parts and percentages are by weight, and are based on the weight at the particular stage of the processing being described.

Example 1

The composition of the present invention contains at least one surfactant from the class of nonionic siloxane alkoxylates (a), and at least one surfactant from the class of aminoalkyleneoxide surfactants (b).

a. Nonionic Siloxane Alkoxylates

Tables 1 and 2 describes the trisiloxane alkoxylates used herein as illustrative examples of the compositions of the present invention. They have the following structure:

$(CH_3)_3Si\text{—}O\text{—}Si(CH_3)(Q)\text{—}O\text{—}Si(CH_3)_3$

TABLE 1

| Reference | Nominal Formula of the Z Group |
|---|---|
| TSA-1 | $C_3H_6O(C_2H_4O)_8CH_3$, Silwet L-77 ® Surfactant |
| TSA-2 | $C_3H_6O(C_2H_4O)_8OH$, Silwet ® 408 | b. Aminoalkyleneoxide Surfactants

Table 2 provides structural information on the aminoalkyleneoxide surfactants components of this instant invention. The aminopolyalkyleneoxide surfactants may be blocked, or random alkyleneoxide groups.

TABLE 2

Description of Conventional Aminoalkyleneoxide Surfactants

| Reference | MW | Wt % EO | Configuration of EO/PO |
|---|---|---|---|
| AAO-1 | 1,650 | 40 | Terminal EO Block |
| AAO-2 | 3,600 | 10 | Terminal EO Block |
| AAO-3 | 5,500 | 40 | Terminal EO Block |
| AAO-4 | 6,700 | 40 | Terminal EO Block |
| AAO-5 | 25,000 | 80 | Terminal EO Block |
| AAO-6 | 30,000 | 80 | Terminal EO Block |
| AAO-7 | 4580 | 10 | Terminal PO Block |

Comparative Nonsilicone Surfactants

Table 3 provides descriptions of a typical, comparative, nonsilicone surfactant, used as an agricultural wetting agent.

TABLE 3

Description of Comparative Conventional Nonsilicone Surfactant

| Ref. | MW | Wt % EO | Remarks |
|---|---|---|---|
| PAO-A | 2150 | 20 | Pluronic ® 17R2 (BASF Corp.), polyalkyleneoxide block copolymer surfactant (PO-EO-PO type). |

TABLE 3-continued

Description of Comparative Conventional Nonsilicone Surfactant

| Ref. | MW | Wt % EO | Remarks |
|---|---|---|---|
| PAO-B | 2500 | 20 | Pluronic ® L-62 (BASF Corp.), polyalkyleneoxide block copolymer surfactant (EO-PO-EO type). |
| OPE | NA | 10 | Octylphenol ethoxylate (TRITON ® X-100) (Union Carbide Corp.) |
| TAE | NA | 5 | Tallow amine ethoxylate (ETHOMEEN ® T/15) (Akzo Nobel) |

Example 2

Spreading

This example demonstrates that the surfactant blend compositions of the present invention are favorable in their ability to provide spreading properties equivalent to the commonly used PAO-A/TSA-1 blends. Table 4 shows that although the aminoalkyleneoxide surfactants are a unique class of surfactants, these materials do not inhibit the spreading properties of the TSA-1, when compared at equivalent TSA-1 concentrations (compare ID 29–31 with AAO/TSA-1 blends). Additionally, TSA-1 blends, with either OPE or TAE, show a significant reduction in the spreading properties as compared to the compositions of the present invention (Compare ID 32,33 with AAO/TSA-1 blends). Spreading was determined by applying a 10 μL droplet of surfactant solution to a polyester film (3M, Write-On film) and measuring the spread diameter after 30 seconds. The solution was applied with an automatic pipette to provide droplets of reproducible volume. Deionized water that was further purified with a Millipore filtration system was used to prepare the surfactant solutions.

TABLE 4

Comparison of Spreading Properties[a] (@0.1 wt %) of TSA-1/Cosurfactant Blends

| ID | Co-surfactant | Composition of Invention | Wt % TSA-1 | Wt % Cosurfactant | Spread Diameter (mm) |
|---|---|---|---|---|---|
| 1 | AAO-1 | No | 0 | 0.1 | 6 |
| 2 | AAO-1 | Yes | 0.025 | 0.075 | 22 |
| 3 | AAO-1 | Yes | 0.05 | 0.05 | 29 |
| 4 | AAO-1 | Yes | 0.075 | 0.025 | 39 |
| 5 | AAO-2 | No | 0 | 0.1 | 7 |
| 6 | AAO-2 | Yes | 0.025 | 0.075 | 19 |
| 7 | AAO-2 | Yes | 0.05 | 0.05 | 36 |
| 8 | AAO-2 | Yes | 0.075 | 0.025 | 43 |
| 9 | AAO-4 | No | 0 | 0.1 | 6 |
| 10 | AAO-4 | Yes | 0.025 | 0.075 | 24 |
| 11 | AAO-4 | Yes | 0.05 | 0.05 | 35 |
| 12 | AAO-4 | Yes | 0.075 | 0.025 | 44 |
| 13 | AAO-5 | No | 0 | 0.1 | 6 |
| 14 | AAO-5 | Yes | 0.025 | 0.075 | 21 |
| 15 | AAO-5 | Yes | 0.05 | 0.05 | 35 |
| 16 | AAO-5 | Yes | 0.075 | 0.025 | 45 |
| 17 | AAO-6 | No | 0 | 0.1 | 7 |
| 18 | AAO-6 | Yes | 0.025 | 0.075 | 22 |
| 19 | AAO-6 | Yes | 0.05 | 0.05 | 35 |
| 20 | AAO-6 | Yes | 0.075 | 0.025 | 43 |
| 21 | AAO-7 | No | 0 | 0.1 | 7 |
| 22 | AAO-7 | Yes | 0.025 | 0.075 | 29 |
| 23 | AAO-7 | Yes | 0.05 | 0.05 | 40 |
| 24 | AAO-7 | Yes | 0.075 | 0.025 | 52 |
| 25 | PAO-A | No | 0 | 0.1 | 7 |
| 26 | PAO-A | No | 0.025 | 0.075 | 27 |
| 27 | PAO-A | No | 0.05 | 0.05 | 35 |
| 28 | PAO-A | No | 0.075 | 0.025 | 45 |

TABLE 4-continued

Comparison of
Spreading Properties[a] (@0.1 wt %) of TSA-1/Cosurfactant Blends

| ID | Co-surfactant | Composition of Invention | Wt % TSA-1 | Wt % Cosurfactant | Spread Diameter (mm) |
|---|---|---|---|---|---|
| 29 | None | N/A | 0.025 | 0 | 20 |
| 30 | None | N/A | 0.050 | 0 | 31 |
| 31 | None | N/A | 0.075 | 0 | 40 |
| 32 | OPE | No | 0.05 | 0.05 | 20 |
| 33 | TAE | No | 0.05 | 0.05 | 8 |
| 34 | None | N/A | 0 | 0 | 4 |

[a]Spreading of 0.1 wt % solution on polyester film.

Example 3

The effect of adjuvant on glyphosate efficacy was determined using a barley regrowth assay. Glyphosate treatments, with and without adjuvant, were sprayed on barley (14–16 cm tall) at rates of 0.125, 0.25 and 0.5 lbs ae/acre. Six hours after application, all plants were trimmed to 2 cm in height, removing 95% of the treated area. Regrowth was assessed 1 week after treatment by measuring fresh weight and plant height. The data are reported as percent inhibition as compared to the untreated control.

Table 5 demonstrates that overall the compositions of the present invention (AAO/TSA-2 combinations) provide enhanced glyphosate efficacy relative to the PAO-B/TSA-2 blend, or as compared to glyphosate without surfactant.

TABLE 5

Summary of Surfactant Effects on Glyphosate Activity

| ID | Surfactant | Composition of Invention | Glyphosate lb ae/acre | % Inhibition Fresh Wt. |
|---|---|---|---|---|
| 22 | AAO-1/TSA-2 | Yes | 0.5 | 57.2 |
| 23 | AAO-1/TSA-2 | Yes | 0.25 | 23.2 |
| 24 | AAO-1/TSA-2 | Yes | 0.175 | 14.4 |
| 32 | AAO-2/TSA-2 | Yes | 0.5 | 70.3 |
| 33 | AAO-2/TSA-2 | Yes | 0.25 | 52.5 |
| 34 | AAO-2/TSA-2 | Yes | 0.175 | 2.6 |
| 35 | AAO-3/TSA-2 | Yes | 0.5 | 72.5 |
| 36 | AAO-3/TSA-2 | Yes | 0.25 | 25.2 |
| 37 | AAO-3/TSA-2 | Yes | 0.175 | 12.2 |
| 38 | AAO-7/TSA-2 | Yes | 0.5 | 79.4 |
| 39 | AAO-7/TSA-2 | Yes | 0.25 | 41.8 |
| 40 | AAO-7/TSA-2 | Yes | 0.175 | 10.3 |
| 41 | PAO-B/TSA-2 | No | 0.5 | 49.8 |
| 42 | PAO-B/TSA-2 | No | 0.25 | 43.8 |
| 43 | PAO-B/TSA-2 | No | 0.125 | 21.4 |
| 44 | None | N/A | 0.5 | 39.7 |
| 45 | None | N/A | 0.25 | 20.2 |
| 46 | None | N/A | 0.125 | 0.6 |

I claim:

1. A pesticidal adjuvant composition comprising
   a. a pesticidal adjuvant effective amount of a nonionic siloxane of the formula:

$$R^5Me_2SiO[Me_2SiO]_f[MeSi(Q)O]_gSiMe_2R^5$$

wherein f=0 to 1, g=1 to 2, $Q=C_dH_{2d}O(C_2H_4O)_t(C_3H_6O)_wR^4$, d=2 to 4, t=3 to 12, w=0 to 8, $R^4$ is hydrogen, acetyl or a hydrocarbon radical containing 1 to 4 carbon atoms, and $R^5$ is Q, alkyl of one to four carbons or a hydroxyl group; and b. a pesticidal adjuvant effective amount of an aminopolyalkyleneoxide of the formula $$(H(R^T)_T)_2NC_2H_4N\ ((R^T)_TH)_2$$

wherein $R^T$ denotes alkoxy groups containing 2 or 3 carbon atoms each, and the subscript T is selected so that the molecular weight of the alkoxylated diamine is 1,000 to 15,000.

2. A composition according to claim 1 wherein the weight ratio of component a. to component b. is 1:99 to 99:1.

3. A composition acording to claim 1 additionally comprising an acid functional pesticide.

4. A composition according to claim 3 where the acid functional pesticide is selected from: growth regulators, photosynthesis inhibitors, pigment inhibitors, mitotic disrupters, lipid biosynthesis inhibitors, cell wall inhibitors, and cell membrane disrupters.

5. A composition according to claim 3 wherein the pesticide is a herbicide selected from the group consisting of: phenoxy acetic acids, phenoxy propionic acids, phenoxy butyric acids, benzoic acids, triazines and s-triazines, substituted ureas, uracils, bentazon, desmedipham, methazole, phenmedipham, pyridate, amitrole, clomazone, fluridone, norflurazone, dinitroanilines, isopropalin, oryzalin, pendimethalin, prodiamine, trifluralin, glyphosate, glufosinate, sulfonylureas, imidazolinones, clethodim, diclofop-methyl, fenoxaprop-ethyl, fluazifop-p-butyl, haloxyfop-methyl, quizalofop, sethoxydim, dichlobenil, isoxaben, and bipyridylium compounds.

6. A process for treating plants comprising applying to plants an effective amount of a composition according to claim 1.

7. A process for treating plants comprising applying to plants an effective amount of a composition according to claim 2.

8. A process for treating plants comprising applying to plants an effective amount of a composition according to claim 3.

9. A process for treating plants comprising applying to plants an effective amount of a composition according to claim 4.

10. A process for treating plants comprising applying to plants an effective amount of a composition according to claim 5.

* * * * *